(12) United States Patent
Kim et al.

(10) Patent No.: US 9,061,285 B2
(45) Date of Patent: Jun. 23, 2015

(54) PCR DEVICE INCLUDING TWO HEATING BLOCKS

(75) Inventors: Sung Woo Kim, Seoul (KR); Duck Joong Kim, Anyang-si (KR); Sun Jin Kim, Seoul (KR); Ho Sun Ryu, Seoul (KR); Dong Hoon Lee, Anyang-si (KR)

(73) Assignee: NANOBIOSYS INC., Seoul (KR)

( * ) Notice: Subject to any disclaimer, the term of this patent is extended or adjusted under 35 U.S.C. 154(b) by 0 days.

(21) Appl. No.: 13/642,877

(22) PCT Filed: Apr. 22, 2011

(86) PCT No.: PCT/KR2011/002911
§ 371 (c)(1),
(2), (4) Date: Oct. 23, 2012

(87) PCT Pub. No.: WO2011/132977
PCT Pub. Date: Oct. 27, 2011

(65) Prior Publication Data
US 2013/0040377 A1   Feb. 14, 2013

(30) Foreign Application Priority Data

Apr. 23, 2010  (KR) .................. 10-2010-0037960
Apr. 21, 2011  (KR) .................. 10-2011-0037352

(51) Int. Cl.
| C12M 3/00 | (2006.01) |
| C12M 1/34 | (2006.01) |
| C12M 1/36 | (2006.01) |
| C12M 1/38 | (2006.01) |
| B01L 7/00 | (2006.01) |
| C12Q 1/68 | (2006.01) |
| B01L 3/00 | (2006.01) |

(52) U.S. Cl.
CPC .............. *B01L 7/5255* (2013.01); *C12Q 1/686* (2013.01); *B01L 3/5027* (2013.01); *B01L 2300/0816* (2013.01); *B01L 2300/1827* (2013.01)

(58) Field of Classification Search
CPC ................ B01L 2300/0816; B01L 2300/1827; B01L 3/5027; B01L 7/5255; C12Q 1/686
USPC ........................................... 435/283.1–309.4
See application file for complete search history.

(56) References Cited

U.S. PATENT DOCUMENTS

| 5,525,300 | A  | * | 6/1996  | Danssaert et al. ............ 422/552 |
| 5,819,842 | A  |   | 10/1998 | Potter et al. |
| 2002/0114734 | A1 | * | 8/2002  | Pantoliano et al. ............ 422/67 |
| 2004/0043479 | A1 | * | 3/2004  | Briscoe et al. ............ 435/288.5 |
| 2004/0106145 | A1 |   | 6/2004  | Gold et al. |
| 2004/0265884 | A1 | * | 12/2004 | Knoche ............................ 435/6 |

(Continued)

FOREIGN PATENT DOCUMENTS

| CN | 101363001 A | 2/2009 |
| CN | 101948741 A | 1/2011 |

(Continued)

OTHER PUBLICATIONS

Dae-Sik Lee, et al., Bulk-Micromachined Submicroliter-Volume . . . , Lab Chip, vol. 4, pp. 401-407, 2004.

*Primary Examiner* — Nathan Bowers
*Assistant Examiner* — Lydia Edwards
(74) *Attorney, Agent, or Firm* — Novick, Kim and Lee, PLLC

(57) ABSTRACT

According to the present invention, a PCR device including two heating blocks which is used for nucleic acid amplification reactions is disclosed. Using the PCR device of the present invention, nucleic acid amplification reactions can be efficiently performed.

14 Claims, 2 Drawing Sheets

(56) References Cited

U.S. PATENT DOCUMENTS

| | | | |
|---|---|---|---|
| 2006/0046304 A1 | 3/2006 | Shigeura et al. | |
| 2007/0292941 A1* | 12/2007 | Handique et al. | 435/288.7 |
| 2008/0176290 A1 | 7/2008 | Joseph et al. | |
| 2009/0042737 A1* | 2/2009 | Katz et al. | 506/10 |
| 2009/0053801 A1* | 2/2009 | Miao et al. | 435/289.1 |
| 2009/0298129 A1* | 12/2009 | Spence et al. | 435/91.2 |
| 2010/0227383 A1* | 9/2010 | Amano et al. | 435/287.2 |
| 2011/0104703 A1 | 5/2011 | Maeda et al. | |
| 2011/0124524 A1* | 5/2011 | Ermakov | 506/16 |

FOREIGN PATENT DOCUMENTS

| | | | |
|---|---|---|---|
| EP | 2145949 A1 | | 1/2010 |
| JP | H6-277036 A | | 10/1994 |
| JP | 2002306154 A | * | 10/2002 |
| JP | 2010-002353 A | | 1/2010 |
| KR | 10-2006-0116983 A | | 11/2006 |
| KR | 10-2006-0116984 A | | 11/2006 |
| KR | 1020060116983 | | 11/2006 |
| KR | 1020060116984 | | 11/2006 |
| KR | 1020100008476 | | 1/2010 |
| WO | 97/40939 A1 | | 11/1997 |
| WO | 97/48818 A1 | | 12/1997 |
| WO | 2006/116616 A2 | | 11/2006 |
| WO | 2008/004695 A1 | | 1/2008 |
| WO | 2009/005001 A1 | | 1/2009 |

* cited by examiner

PCR DEVICE INCLUDING TWO HEATING BLOCKS

CROSS-REFERENCE TO RELATED APPLICATIONS

This application is 371 of PCT/KR2011/002911 filed on Apr. 22, 2011, which claims the benefit of priority from Korean Patent Applications Nos. 10-2010-0037960 and 10-2011-0037352, filed on Apr. 23, 2010 and Apr. 21, 2011, respectively, the contents of each of which are incorporated herein by reference in its entirety.

TECHNICAL FIELD

The present invention relates to a polymerase chain reaction (PCR) device including a heating block which is used for nucleic acid amplification.

BACKGROUND ART

Polymerase chain reaction (PCR) is a technique of repeatedly heating and cooling a sample solution including nucleic acid to chain-replicate a region of the nucleic acid having a specific base sequence and thus to exponentially amplify the nucleic acid having the specific base sequence region and is commonly used in the fields, such as life science, genetic engineering, and medicine, for analysis and diagnosis.

Recently, various PCR devices have been developed to perform the PCR. A PCR device according to an example is installed with a container including a sample solution including nucleic acid in one reaction chamber and performs the PCR by repeatedly heating and cooling the container. Although an overall structure is not complicated since the PCR device of the example includes one reaction chamber, complicated circuits need to be included for accurate temperature control, and a total time for the whole PCR may be extended due to the repeated heating and cooling of one reaction chamber. Also, a PCR device according to another example is installed with a plurality of reaction chambers at a temperature for the PCR and performs the PCR by allowing a sample solution, including nucleic acid, to flow via one channel which passes through the reaction chambers. Although complicated circuits for accurate temperature control are not needed as the PCR device of another example uses a plurality of reaction chambers, a long flow channel that passes through the reaction chambers having high and low temperatures is necessary, and thus, an overall structure may be complicated, and a separate control device is required to control a flow rate of the sample solution, including nucleic acid, which flows via the channel that passes through the reaction chambers.

Therefore, a PCR device that may have a simple overall structure, minimize a total PCR reaction time, and obtain reliable PCR yield is desired.

DETAILED DESCRIPTION OF THE INVENTION

Technical Problem

The present invention provides a polymerase chain reaction (PCR) device exhibiting excellent performance in a nucleic acid amplification reaction.

Technical Solution

According to an aspect of the present invention, there is provided a polymerase chain reaction (PCR) device including a first heating block disposed on a substrate; a second heating block disposed separate from the first heating block on the substrate; a chip holder that is capable of being moved left-right and/or up-down by a driving means over the first and second heating blocks, and is installed with a chip for PCR.

A heating wire may be disposed in each of the first and second heating blocks.

The heating wire may be disposed symmetrically in up-down and/or left-right directions based on a center of each surface of the first and second heating blocks to evenly maintain an overall temperature inside the first or second heating block.

The first and second heating blocks may be manufactured to maintain a denaturing temperature of the PCR.

The denaturing temperature may be from about 90° C. to about 100° C.

The first and second heating blocks may be manufactured to maintain an annealing and extension (or amplification) temperature of the PCR.

The annealing and extension (or amplification) temperature may be from about 55° C. to about 75° C.

The first and second heating blocks may replace each other.

The first and second heating blocks may be separately disposed at a predetermined distance so that heat exchange therebetween does not occur.

The driving means may include a rail that extends in the left-right direction; and a connection member that is disposed as to enable a sliding motion in the left-right direction via the rail and enables a sliding motion in the up-down direction, wherein the chip holder is disposed at an end of the connection member.

The chip for PCR may be detachable from the chip holder.

The chip for PCR may be in contact with the first heating block or the second heating block and contain a sample solution including nucleic acid to be amplified.

The chip for PCR may be a light transmitting plastic material.

The PCR chip may include a first plate; a second plate that is disposed on the first plate and includes a through opening channel; and a third plate that is disposed on the second plate and includes a through opening inlet unit, which is formed with respect to a portion of the through opening channel formed, and a through opening outlet unit, which are formed with respect to the other portion of the through opening channel.

The first and third plates may include a material selected from the group consisting of polydimethylsiloxane (PDMS), cyclic olefin copolymer (COC), polymethyl methacrylate (PMMA), polycarbonate (PC), polypropylene carbonate (PPC), polyether sulfone (PES), polyethylene terephthalate (PET), and a combination thereof, and the second plate may include a thermoplastic or thermosetting resin material selected from the group consisting of polymethyl methacrylate (PMMA), polycarbonate (PC), COC, polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutylene terephthalate (PBT), fluorinated ethylene propylene (FEP), perfluoro alkoxyalkane (PFA), and a combination thereof.

A diameter of the through opening inlet unit of the third plate may be selected from about 1.0 mm to about 3.0 mm, a diameter of the through opening outlet unit is selected from about 1.0 mm to about 1.5 mm, a thickness of the third plate is selected from about 0.1 mm to about 2 mm, a thickness of the second plate is selected from about 100 µm to about 200

μm, a width of the through opening channel is selected from about 0.5 mm to about 3 mm, and a length of the through opening channel is selected from about 20 mm to about 40 mm.

A light source may be further interposed between the first and second heating blocks, and a light detection unit for detecting the light emitted from the light source is further disposed on the chip holder; or the light detection unit for detecting the light emitted from the light source is further interposed between the first and second heating blocks, and the light source is further disposed on the chip holder.

The light detection unit may be disposed on the driving means, and a transmission unit for transmitting the light emitted from the light source is disposed in the driving means.

Advantageous Effects

As PCR device including two heating blocks according to the present invention is provided, nucleic acid amplification reactions may be effectively performed.

BEST MODE

Hereinafter, exemplary embodiments of the present invention will be described in greater detail with reference to the attached drawings.

Figure 1:
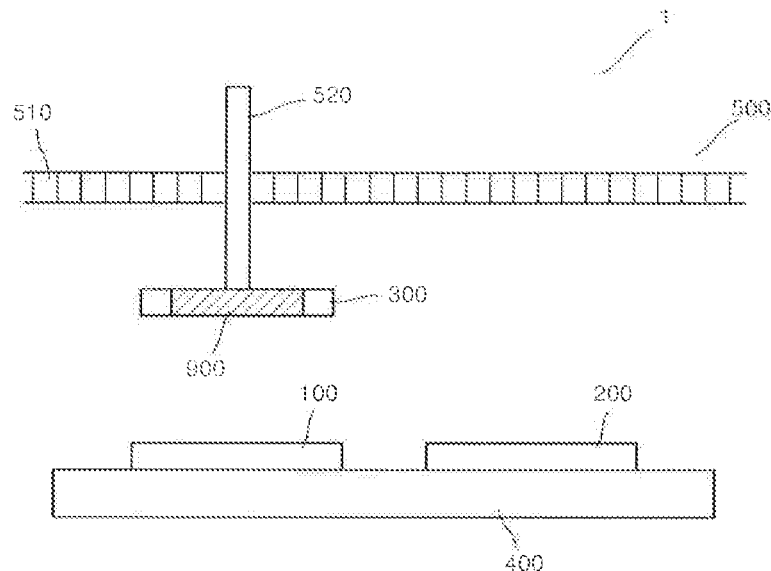
FIG. 1 illustrates a PCR device including two heating blocks according to an embodiment of the present invention.

FIG. 1 illustrates a PCR device 1 including two heating blocks according to an embodiment of the present invention.

The PCR device 1 according to an embodiment of the present invention includes a first heating block 100 disposed on a substrate 400; a second heating block 200 disposed separate from the first heating block 100 on the substrate 400; and a chip holder 300 that is capable of being moved left-right and/or up-down by a driving means 500 over the first and second heating blocks 100 and 200, and is installed with a chip for PCR 900.

The PCR device 1 is a device that is used in the PCR (Polymerase Chain Reaction) to amplify nucleic acid having a specific base sequence. For example, a PCR device for amplification of DNA (deoxyribonucleic acid) having a specific base sequence performs three steps: denaturing, annealing, and extension, and the DNA having the specific base sequence may be exponentially amplified by repeating, for example, 20 to 40 cycles of the three steps: the denaturing step involves heating a sample solution including double-stranded DNA to a predetermined temperature, for example about 95, to separate the double-stranded DNA into single-stranded DNA; the annealing step involves providing oligonucleotide primers having a sequence complementary to the specific base sequence to be amplified to the sample solution, cooling the separated single-stranded DNA along with the primers to a predetermined temperature, for example 55, and thus binding the primers to a specific base sequence of the single-stranded DNA, thereby forming a partially DNA-primer complex; and the extension (or amplification) step involves maintaining a temperature of the sample solution after the annealing step at an appropriate temperature, for example 72, and thus forming double-stranded DNA by the action of DNA polymerase based on primers of the partially DNA-primer complex. Also, in some embodiments, the PCR device may perform the annealing step and the extension (or amplification) step at the same time, and in this regard, the PCR may complete one cycle by performing a two-step process consisting of the annealing step and the annealing and extension (or amplification) step. Therefore, the PCR device 1 according to an embodiment of the present invention refers to a device including modules for performing the steps stated above, and the modules not stated herein in detail are assumed as if they are all included within the obvious scope disclosed in the prior art for performing PCR.

The PCR device 1 according to an embodiment of the present invention includes the first heating block 100 disposed on the substrate 400 and the second heating block 200 disposed separate from the first heating block 100 on the substrate 400.

The substrate 400 includes any material having physical and/or chemical properties that do not change due to heating or maintaining the temperature of the first heating block 100 and the second heating block 200 and via which heat exchange between the first heating block 100 and the second heating block 200 does not occur. For example, the substrate 400 may include a material such as plastic or may be formed of such material.

The first heating block 100 and the second heating block 200 are disposed to maintain a temperature for performing the denaturing, annealing, and extension (or amplification) steps to amplify nucleic acid. Thus, the first heating block 100 and the second heating block 200 may provide a necessary temperature required in each of the steps and may include various modules for maintaining the temperature or may be drivably connected to the modules. Thus, when the chip holder 300 installed with the chip for PCR 900 contacts a surface of one of the first and second heating blocks 100 and 200, a sample solution in the chip for PCR 900 may be evenly heated and maintained at a desired temperature since the entire surface of the first heating block 100 or the second heating block 200 in contact with the chip for PCR 900 may be heated or maintained at a desired temperature. Unlike a conventional PCR device using a single heating block has a rate of temperature change of the single heating block in a range of 3 to 7 per second, the PCR device 1 including the two heating blocks according to an embodiment of the present invention may significantly reduce a PCR time as a rate of temperature change of each of the first and second heating blocks 100 and 200 may be in a range of 20 to per second.

A heating wire (not shown) may be disposed in each of the first and second heating blocks 100 and 200. The heating wire may be drivably connected to various heat sources to maintain a temperature for performing the denaturing, annealing, and extension (or amplification) steps or may be drivably connected to various temperature sensors to monitor a temperature of the heating wire. The heating wire may be disposed symmetrically in up-down and/or left-right directions based on a center of each surface of the first and second heating blocks 100 and 200 to evenly maintain an overall temperature inside the first and second heating blocks 100 and 200. An arrangement of the heating wire symmetrical in up-down and/or left-right directions may vary. Also, thin film heaters (not shown) may be disposed inside the first or second heating block 100 or 200. The thin film heaters may be separately disposed with a regular distance in up-down and/or left-right directions based on a center of each surface of the first and second heating blocks 100 and 200 to evenly maintain an overall temperature inside the first and second heating blocks 100 and 200. A regular arrangement of the thin film heaters in up-down and/or left-right directions may vary.

The first and second heating blocks 100 and 200 may include a metal material, for example, may include an aluminum material or may be formed of an aluminum material, for even heat distribution and rapid heat transfer to the same area.

The first heating block 100 may be manufactured to maintain an appropriate temperature for performing the denaturing step, or the annealing and extension (or amplification) step. For example, the first heating block 100 of the PCR device 1 according to an embodiment of the present invention may maintain a temperature from 50 to 100, may maintain a temperature from 90 to 100, preferably 95, when the denaturing step is performed at the first heating block 100, or may maintain a temperature from 55 to about 75, preferably 72, when the annealing and extension (or amplification) step is performed at the first heating block. However, the temperature is not limited thereto as long as the denaturing step, or the annealing and extension (or amplification) step may be performed. The second heating block 200 may be manufactured to maintain an appropriate temperature for performing the denaturing step or the annealing and extension (or amplification) step. For example, the second heating block 200 of the PCR device 1 according to an embodiment of the present invention may maintain a temperature from 90 to 100, preferably 95, when the denaturing step is performed at the second heating block 200, or may maintain a temperature from 55 to 75, preferably 72, when the annealing and extension (or amplification) step is performed at the second heating block 200. However, the temperature is not limited thereto as long as the denaturing step or the annealing and extension (or amplification) step may be performed. Therefore, according to an embodiment of the present invention, the first heating block 100 may maintain a denaturing temperature of PCR. When a denaturing temperature is lower than 90, the nucleic acid that forms a template for the PCR is denatured, yielding a decrease in efficiency of the PCR, thus a PCR efficiency may be decreased or the PCR may not occur. Also, when a denaturing temperature is higher than 100, an enzyme used in the PCR may lose its activity, thus the denaturing temperature may be from 90 to 100, preferably 95. Also, according to an embodiment of the present invention, the second heating block 200 may maintain an annealing and extension (or amplification) temperature of PCR. When the annealing and extension (or amplification) temperature is lower than 55, specificity of the PCR product may be decreased, and when the annealing and extension (or amplification) temperature is higher than 74, a PCR efficiency may be decreased as an extension due to the primers may not occur, thus the annealing and extension (or amplification) temperature may be from 55 to 75, preferably 72.

The first and second heating blocks 100 and 200 may be separately disposed at a predetermined distance so that heat exchange therebetween may not occur. Accordingly, since heat exchange between the first heating block 100 and second heating block 200 does not occur, accurate temperature control at the denaturing step and the annealing and extension (or amplification) step may be enabled in a nucleic acid amplification reaction which may be significantly affected by a slight temperature change.

The PCR device 1 according to an embodiment of the present invention includes a chip holder 300 that is capable of being moved left-right and/or up-down by a driving means 500 over the first and second heating blocks 100 and 200, and is installed with a chip for PCR 900. Also, the chip for PCR 900 may be manufactured to contact a surface of the first heating block 100 or the second heating block 200 and to contain a sample solution including nucleic acid to be amplified.

The chip for PCR 900 may contain a sample solution including nucleic acid, such as double-stranded DNA, oligonucleotide primers having a sequence complementary to a specific base sequence to be amplified, DNA polymerase, deoxyribonucleotide triphosphates (dNTP), or a PCR reaction buffer. The chip for PCR 900 may include an inlet unit (not shown) for introducing the sample solution, an outlet unit (not shown) for withdrawing the sample solution that completed the nucleic acid amplification reaction, and a reaction chamber (or channel) (not shown) where the nucleic acid amplification reaction of the sample solution is performed. When the chip for PCR 900 is in contact with the first and second heating block 100 and 200, heat of the first and second heating block 100 and 200 is transferred to the chip for PCR 900, and thus the sample solution included in the reaction chamber (or channel) of the chip for PCR 900 may be heated and maintained at a temperature. Also, the chip for PCR 900 may have an overall planar shape, but is not limited thereto. Moreover, when the nucleic acid amplification reaction is performed by the PCR device 1, an outer wall of the PCR chip 900 may have a shape and structure for the chip for PCR 900 to be fixed in an inner space of the chip holder 300 so that the chip for PCR 900 does not dissociate from the chip holder 300. A detailed description of the chip for PCR 900 will be described hereinafter with reference to FIGS. 4 and 5.

The chip holder 300 is a module for the chip for PCR 900 to be installed in the PCR device 1. When the nucleic acid amplification reaction is performed by the PCR device 1, an inner wall of the chip holder 300 may have a shape and structure for the chip for PCR 900 to be fixed on the outer wall of the chip for PCR 900 so that the chip for PCR 900 does not dissociate from the chip holder 300. The chip holder 300 may be drivably connected to the driving means 500. Also, the chip for PCR 900 may be detachable from the chip holder 300.

The driving means 500 includes all means enabling the chip holder 300 installed with the chip for PCR 900 to move left-right and/or up-down over the first and second heating blocks 100 and 200. As the driving means 500 moves left-right, the chip holder 300 installed with the chip for PCR 900 may move back and forth between the first heating block 100 and second heating block 200, and as the driving means 500 moves up-down, the chip holder 300 installed with the chip for PCR 900 may be in contact with and be separated from the first and second heating block 100 and 200. As shown in FIG. 1, the driving means 500 of the PCR device 1 according to an embodiment of the present invention includes a rail 510 that extends in the left-right direction and a connection member 520 that is disposed as to enable a sliding motion in the left-right direction via the rail 510 and enable a sliding motion in the up-down direction, wherein the chip holder 300 is disposed at an end of the connection member 520. The left-right and/or up-down movement of the driving means 500 may be controlled by a controlling means (not shown) drivably disposed inside or outside of the PCR device 1, and the controlling means may control the contact and separation between the chip holder 300 installed with the chip for PCR 900 for denaturing step and annealing and extension (or amplification) step of PCR and the first or second heating block 100 or 200.

Figure 2:
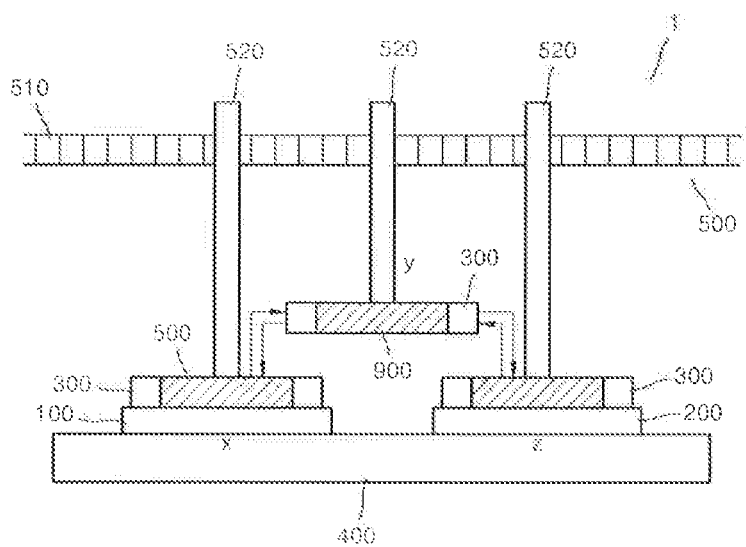
FIG. 2 illustrates each step of nucleic acid amplification reaction due to movement of a chip holder of the PCR device according to an embodiment of the present invention.

FIG. 2 illustrates each step of the nucleic acid amplification reaction due to the movement of the chip holder of the PCR device according to an embodiment of the present invention.

The nucleic acid amplification reaction due to the PCR device 1 according to an embodiment of the present invention has the following steps: First, a sample solution including nucleic acid, such as double-stranded DNA, oligonucleotide primers having a sequence complementary to a specific base sequence to be amplified, DNA polymerase, dNTP, or a PCR reaction buffer, is introduced to the chip for PCR 900, the chip for PCR 900 may be installed in the chip holder 300. Next or at the same time, the first heating block 100 may be heated up to a temperature for the denaturing step, for example 90 to 100, and maintained at the temperature, preferably heated up to 95 and maintained at the temperature. The second heating block 200 may be heated up to a temperature for the annealing and extension (or amplification) step, for example 55 to 75, and maintained at the temperature, preferably heated up to 72 and maintained at the temperature.

Then, the connection member 520 of the driving means 500 may be controlled to move the chip for PCR 900 downward, thus the chip holder 300 installed with the chip for PCR 900 may be in contact with the first heating block 100 to perform a first denaturing step (step x) of PCR.

Subsequently, the connection member 520 of the driving means 500 may be controlled to move the chip for PCR 900 upward, thus the chip holder 300 installed with the chip for PCR 900 may be separated from the first heating block 100 to terminate the first denaturing step of PCR, the connection member 520 of the driving means 500 may be controlled to perform a step to move the chip for PCR 900 above the second heating block 200 (step y).

Next, the connection member 520 of the driving means 500 may be controlled to move the chip for PCR 900 downward, thus the chip holder 300 installed with the chip for PCR 900 may be in contact with the second heating block 100 to perform the first annealing and extension (or amplification) step of PCR (step z).

Lastly, the connection member 520 of the driving means 500 may be controlled to move the chip for PCR 900 upward, thus the chip holder 300 installed with the chip for PCR 900 may be separated from the second heating block 100 to terminate the first annealing and extension (or amplification) step of PCR, the connection member 520 of the driving means 500 may be controlled to move the chip for PCR 900 above the first heating block 100 and repeat the steps x, y, and z, thereby performing the nucleic acid amplification reaction (circulating step).

Figure 3:
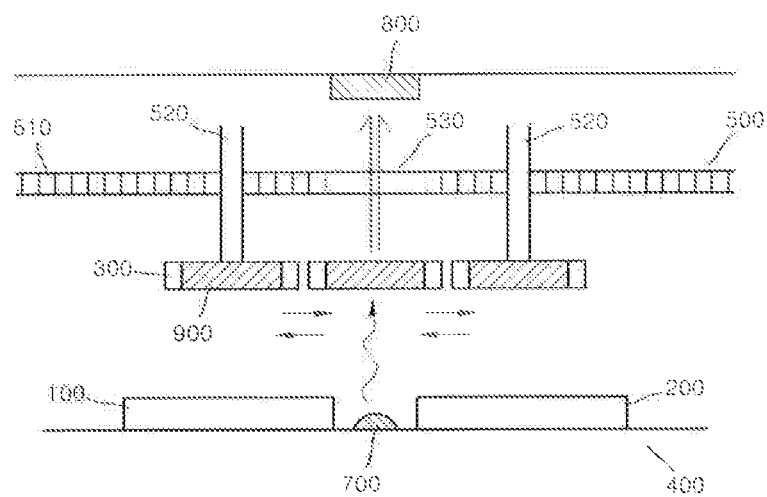
FIG. 3 illustrates steps of detecting nucleic acid amplification reaction in real time using the PCR device according to an embodiment of the present invention.

FIG. 3 illustrates steps of monitoring the nucleic acid amplification reaction in real-time using the PCR device according to an embodiment of the present invention.

In the PCR 1 device according to an embodiment of the present invention, a light source 700 is further interposed between the first and second heating blocks 100 and 200, and a light detection unit 800 for detecting the light emitted from the light source 700 is further disposed above the chip holder 300; or the light detection unit 800 for detecting the light emitted from the light source 700 is further interposed between the first and second heating blocks 100 and 200, and the light source 700 is further disposed above the chip holder 300. Also, the light detection unit 800 may be disposed above the driving means 500, and a transmission unit 530 for transmitting the light emitted from the light source 700 may be disposed in the driving means 500. Also, the chip for PCR 900 may be a light transmitting material, particularly a light transmitting plastic material. The detailed description of the chip for PCR 900 will be described hereinafter with reference to FIGS. 4 and 5.

During the nucleic acid amplification reaction due to the PCR device 1 according to an embodiment of the present invention, a degree of the nucleic acid being amplified in the chip for PCR 900 may be detected in real time by disposing the light source 700 and the light detection unit 800. For detecting the degree of the nucleic acid being amplified in the chip for PCR, a separate fluorescent material may be further added to the sample solution that is introduced to the chip for PCR 900. The light source 700 is disposed to distribute over the separate space between the first and second heating blocks 100 and 200 as wide as possible and is disposed to emit possibly the same light. The light source 700 may be connected and disposed to be drivable with a lens (not shown) collecting the light emitted from the light source 700 and a light filter (not shown) filtering light at a range of particular wavelengths.

During the nucleic acid amplification reaction due to the PCR device 1 according to an embodiment of the present invention, steps of detecting the degree of the nucleic acid being amplified in the chip for PCR 900 in real time are as follows. When the connection member 520 of the driving means 500 is controlled to move the chip for PCR 900 from above the first heating block 100 to above the second heating block 200 after completing the first denaturing step of the PCR, or when the connection member 520 of the driving means 500 is controlled to move the chip for PCR 900 from above the second heating block 200 to above the first heating block 100 after completing the first annealing and extension (or amplification) step of the PCR, the connection member 520 of the driving means 500 is controlled to stop the chip holder 300 installed with the chip for PCR 900 in the separate space between the first and second heating blocks 100 and 200. Then, light is emitted from the light source 700, the emitted light transmits through the chip for PCR 900 which is light transparent, particularly the reaction chamber (or channel) of the chip for PCR 900, and in this case, a light signal generated by amplification of the nucleic acid inside the reaction chamber (or channel) is detected by the detection unit 800. In this case, the light transmitted through the chip for PCR 900 which is light transparent may arrive at the detection unit 800 by transmitting through the driving means 500, particularly the transmission unit 530 disposed in the rail 510.

Thus, in regard of the PCR device 1 according to an embodiment of the present invention, an amount of target nucleic acid included in an initial reaction sample may be measured and analyzed in real time by monitoring the reaction results due to amplification of the nucleic acid (to which the fluorescent material is attached) in the reaction chamber (or channel) in real time while each of the circulation steps of the PCR proceeds.

Figure 4:
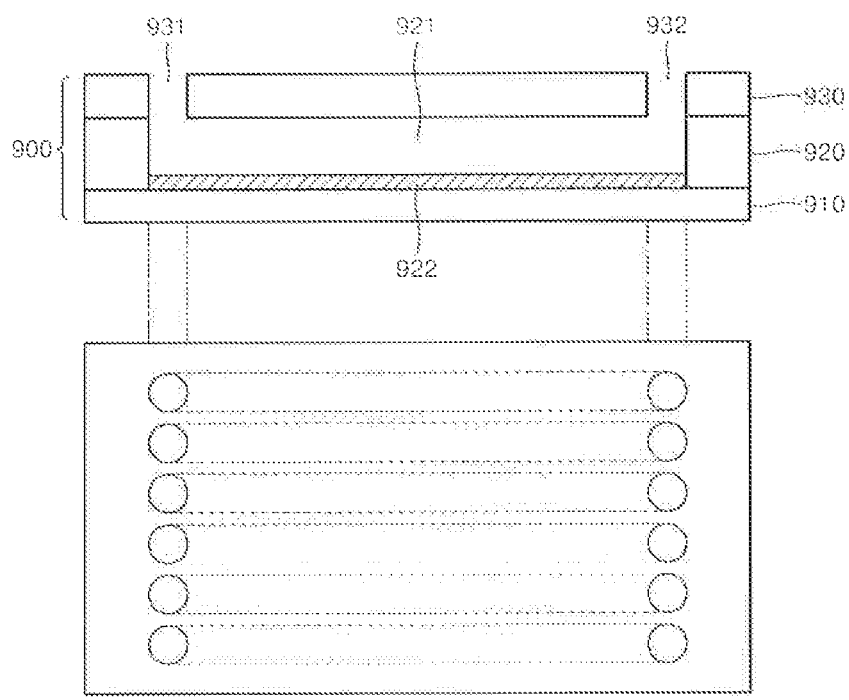
FIG. 4 illustrates a chip for PCR installed in the chip holder of the PCR device according to an embodiment of the present invention.

FIG. 4 illustrates the chip for PCR 900 that is installed in the chip holder 300 of the PCR device 1 according to an embodiment of the present invention.

The chip for PCR 900 may contain a sample solution including nucleic acid, such as double-stranded DNA, oligonucleotide primers having a sequence complementary to a specific base sequence to be amplified, DNA polymerase, dNTP, or a PCR reaction buffer. The chip for PCR 900 may include an inlet unit 931 for introducing the sample solution, an outlet unit 932 for withdrawing the sample solution that completed the nucleic acid amplification reaction, and one or more reaction chambers (or channels) 921 in where the sample solution including nucleic acid to be amplified is contained. When the chip for PCR 900 is in contact with the first heating block 100 or second heating block 200, heat of the first heating block 100 or the second heating block 200 is transferred to the chip for PCR 900, and thus the sample solution included in the reaction chamber (or channel) of the chip for PCR 900 may be heated or cooled and maintained at a constant temperature. Also, the chip for PCR 900 may have an overall planar shape, but is not limited thereto. Moreover, the chip for PCR 900 installed in the chip holder 300 may be disposed in contact with the first or second heating block 100 or 200. Thus, according to an embodiment of the present invention, a fact that the chip for PCR 900 is disposed on one surface of the first or second heating block 100 or 200 may indicate that the chip for PCR 900 installed in the chip holder 300 is disposed in contact with the first or second heating block 100 or 200. Also, the chip for PCR 900 may be formed of a light transmitting material, preferably a light transmitting plastic material. When plastic is used to manufacture the chip for PCR 900, an efficiency of heat transfer may be increased only by controlling a thickness of the plastic, and a cost of manufacture may be decreased as the manufacturing process is simple. Also, since the chip for PCR 900 may include light transmitting properties as a whole, light may be directly irradiated while the chip for PCR 900 is disposed on one surface of the first or second heating block 100 or 200, thus amplification of nucleic acid and a degree of the amplification may be measured and analyzed in real time.

A first plate 910 is disposed on a second plate 920. As the first plate 910 is disposed in contact with a lower surface of the second plate 920, a through opening channel 921 may form a type of PCR chamber. Also, the first plate 910 may be formed of various materials, preferably a material selected from the group consisting of polydimethylsiloxane (PDMS), cycle olefin copolymer (COC), polymethyl methacrylate (PMMA), polycarbonate (PC), polypropylene carbonate (PPC), polyether sulfone (PES), polyethylene terephthalate (PET), and a combination thereof. In addition, a top surface of the first plate 910 is treated with a hydrophilic material 922 so that the PCR may be smoothly performed. A single layer including the hydrophilic material 922 may be formed on the first plate 910 due to the treatment the hydrophilic material 922. The hydrophilic material may be various materials, preferably a material selected from the group consisting of a carboxyl group (—COOH), amine group (—NH$_2$), hydroxyl group (—OH), and sulfone group (—SH), and the treatment the hydrophilic material 922 may be performed using a known method in the art.

The second plate 920 is disposed on the first plate 910. The second plate 920 includes the through opening channel 921. The through opening channels 921 may be connected to a part corresponding to a through opening inlet unit 931 and a through opening outlet unit 932 and form a type of PCR chamber. Thus, PCR is performed after the sample solution to be amplified is introduced in the through opening channel 921. Also, two or more through opening channels 921 may be used depending on a purpose of use and scope of the PCR device 1 according to an embodiment of the present invention. Referring to FIG. 4, 6 through opening channels 921 are illustrated. Moreover, the second plate 920 may be formed of various materials, preferably a thermoplastic resin or thermosetting resin material selected from the group consisting of polymethyl methacrylate (PMMA), polycarbonate (PC), cyclic olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinyl chloride (PVC), polyvinylidene fluoride (PVDF), polybutylene terephthalate (PBT), fluorinated ethylene propylene (FEP), perfluoro alkoxyalkane (PFA), and a combination thereof. Also, a thickness of the second plate 920 may vary, and may be selected from 100 μm to 200 μm. Moreover, a width and length of the through opening channel 921 may vary, preferably a width of the through opening channel 921 may be selected from 0.5 mm to 3 mm, and a length of the through opening channel 921 may be selected from 20 mm to 40 mm. In addition, an inner wall of the second plate 920 may be coated with a material such as silane-based material or bovine serum albumin (BSA), and the coating may be performed using a known method in the art.

The third plate 930 is disposed on the second plate 920. The third plate 930 includes a through opening inlet unit 931, which is formed with respect to a portion of the through opening channel 921 formed in the second plate 920, and a the through opening outlet unit 932, which is formed with respect to the other portion of the through opening channel 921. The through opening inlet unit 931 is a region where the sample solution including the nucleic acid to be amplified is introduced. The through opening outlet unit 932 is a region where the sample solution is withdrawn after completing the PCR. Thus, the third plate 930 covers the through opening channel 921 formed in the second plate 920 which will be described herein, and the through opening inlet unit 931 and the through opening outlet unit 932 serve as an inlet unit and an outlet unit of the through opening channels 921. Also, the third plate 930 may be formed of various materials, preferably a material selected from the group consisting of polydimethylsiloxane (PDMS), cycle olefin copolymer (COC), polymethyl methacrylate (PMMA), polycarbonate (PC), polypropylene carbonate (PPC), polyether sulfone (PES), polyethylene terephthalate (PET), and a combination thereof. Although a size of the through opening inlet unit 931 may vary, preferably a diameter of the through opening inlet unit 931 may be selected from 1.0 mm to 3.0 mm. Also, although a size of the through opening outlet unit 932 may vary, preferably a diameter of the through opening outlet unit 932 may be selected from 1.0 mm to 1.5 mm. Moreover, the through opening inlet unit 931 and the through opening outlet unit 932 include separate cover means (not shown), and thus leakage of the sample solution while the PCR is being performed for the sample solution in the through opening channel 921 may be prevented. The cover means may be formed in various shapes, sizes, or materials. Also, a thickness of the third plate may vary, preferably may be selected from 0.1 mm to 2.0 mm. Moreover, two or more through opening inlet units 931 and through opening outlet units 932 may be used.

Figure 5:
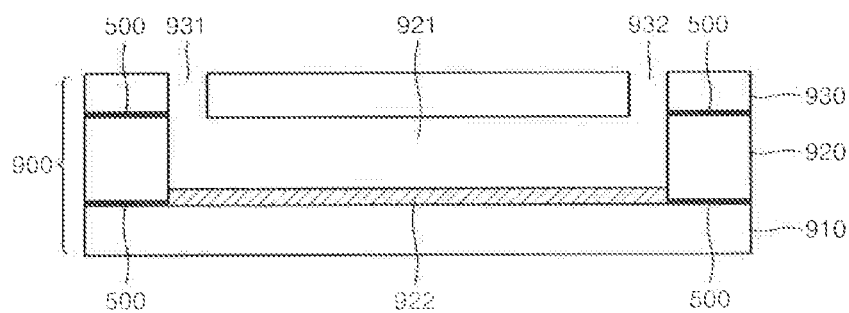
FIG. 5 illustrates a cross-section of the chip for PCR installed in the chip holder of the PCR device according to an embodiment of the present invention which is treated with a double-sided adhesive, thermoplastic resin, or thermosetting resin.

FIG. 5 illustrates a cross-section of the chip for PCR 900 installed in the chip holder 300 of the PCR device according to an embodiment of the present invention which is treated with a double-sided adhesive, thermoplastic resin, or thermosetting resin.

The chip for PCR 900 may be easily manufactured by a method including providing the third plate 930 by forming the through opening inlet unit 931 and the through opening outlet unit 932 through a mechanical process; providing the second plate 920 by forming the through opening channels 921 in a board having a size corresponding to the lower surface of the third plate 930 from the region corresponding to the through opening inlet unit 931 of the third plate 930 to the region corresponding to the through opening outlet unit 932 of the third plate 930 via a mechanical process; providing the first plate 910 by forming a surface treated with the hydrophilic material 922 through a surface treatment process on an upper surface of a board having a size corresponding to the lower surface of the second plate 920; and bonding the lower surface of the third plate 930 to the upper surface of the second plate 920 through a bonding process, and the lower surface of the second plate 920 to the upper surface of the first plate 910 through a bonding process.

The through opening inlet unit 931 and the through opening outlet unit 932 of the third plate 930, and the through opening channel 921 of the second plate 920 may be formed by using a manufacturing method selected from the group consisting of injection molding, hot-embossing, casting, and laser ablation. Also, the hydrophilic material 922 on the surface of the first plate 910 may be treated by a method selected from the group consisting of an oxygen-argon plasma treatment, corona discharge treatment, and surfactant coating, or a known method in the art. Moreover, the lower surface of the third plate 930 and the upper surface of the second plate 920, and the lower surface of the second plate 920 and the upper surface of the first plate 910 may be bonded by using a thermal bonding, ultrasonic welding, or solvent bonding process, or by following a known method in the art. A double-sided tape, thermoplastic resin, or thermosetting resin 500 may be treated between the third plate 930 and the second plate 920, and between the second plate 920 and the third plate 910.

Example

A PCR device of another company which is commonly used and the PCR device according to an embodiment of the present invention shown in FIG. 3 were used to compare and analyze the results of performing a nucleic acid amplification reaction using each of the devices. The PCR device of another company was LightCycler 1.5 available from ROCHE Co., which is constructed of one heating block.

For reliability of the results of the nucleic acid amplification reaction, a sample solution of a positive control and a sample solution of a negative control were each prepared. For the positive control, the sample solution of about 60 μl including 30 μl of 2× SYBR green buffer, 4.4 μl (50 ng/20 μl) of double-stranded template cDNA, pairs of primers complementarily binding to a specific base sequence, particularly 6 μl (1 μmole) of forward primers, 6 μl (1 μmole) of reverse primers, and 13.6 μl of distilled water was prepared, and for the negative control, the sample solution of about 60 μl including 30 μl of 2× SYBR green buffer and 30 μl of distilled water was prepared. Regarding a standard and size of the PCR device according to an embodiment of the present invention different from the PCR device of another company, about 30 μl of the sample solutions were introduced to a chip of PCR is installed in the PCR device of another company, and about 5 μl of the sample solutions were introduced to a chip of PCR is installed in the PCR device according to an embodiment of the present invention.

Under the experimental conditions state above, 20 cycles of PCR were first performed using the PCR device according to an embodiment of the present invention. A temperature of the first heating block was heated up and maintained at 95° C., allowed to vary in a range of 90° C. to 100° C., and a temperature of the second heating block was heated up and maintained at 72° C., allowed to vary in a range of 55° C. to 75° C. The sample solutions of the positive control and negative control were introduced to the chip for PCR, and the chip for PCR was installed in the chip holder of the PCR device. Then, the PCR device was operated. The denaturing step was performed for about 10 seconds, subsequently the annealing and extension (or amplification) step was performed for about 10 seconds, and a fluorescent detection value due to the nucleic acid amplification was measured after every cycle of each step. As a result, the fluorescent detection values showed an increase maintained curve after 5 minutes from the starting point of the PCR device operation. Also, under the experimental conditions, 20 cycles of PCR using the PCR device of another company were performed. As a result, 30 or more minutes were required to reach the fluorescent detection values achieved by the PCR device according to an embodiment of the present invention.

The invention claimed is:

1. A polymerase chain reaction (PCR) device comprising:
   a first heating block disposed on a substrate;
   a second heating block separately disposed from the first heating block on the substrate;
   a first temperature module coupled to a first heating wire to heat and maintain the first heating block at a first temperature in a range from about 90° C. to about 100° C.;
   a second temperature module coupled to a second heating wire to heat and maintain the second heating block at a second temperature in a range from about 55° C. to about 75° C.;
   a chip holder accommodating a chip for PCR;
   a driving unit comprising,
      a rail extending in a first direction between the first heating block and the second heating block, and
      a connection member extending in a second direction and sliding along with the rail, the connection member accommodating the chip holder, wherein the first direction is different from the second direction; and
   a control unit coupled to the driving unit,
   wherein the control unit has a configuration to move the chip holder, by the driving unit, from the first heating block to the second heating block and from the second heating block to the first heating block,
   wherein the control unit has a configuration to place the chip for PCR, by the driving unit, being alternately in contact with the first heating block and the second heating block for a first predetermined period of time for the first heating block and for a second predetermined period of time for the second heating block, and
   wherein each of the first heating block and the second heating block is a single heating block.

2. The PCR device of claim 1, wherein the first heating wire and the second heating wire are symmetrically disposed in up-down and left-right directions on each surface of the first heating block and the second heating block, and the first heating wire and the second heating wire evenly maintain an overall temperature inside each of the first heating wire and the second heating block, respectively.

3. The PCR device of claim 1, wherein the first and second heating blocks are separately disposed on the substrate at a predetermined distance so that heat exchange therebetween does not occur.

4. The PCR device of claim 1, wherein the driving unit comprises:
   the rail extending in a left-right direction; and
   the connection member extending in an up-down direction, wherein the chip holder is disposed at an end of the connection member so that the chip holder is movable in the left-right and/or the up-down direction(s) between the first and second heating blocks.

5. The PCR device of claim 1, wherein the chip for PCR is detachably attached to the chip holder.

6. The PCR device of claim 1, wherein the chip for PCR is configured to contact a surface of the first heating block or the second heating block and to contain a sample solution including nucleic acid to be amplified.

7. The PCR device of claim 1, wherein the chip for PCR includes a light transmitting plastic material.

8. The PCR device of claim 1, wherein the chip for PCR comprises:
a first plate;
a second plate that is disposed on the first plate and comprises a through opening channel; and
a third plate that is disposed on the second plate and comprises:
a through opening inlet unit which is formed with respect to a portion of the through opening channel, and
a through opening outlet unit which is formed with respect to another portion of the through opening channel.

9. The PCR device of claim 8, wherein the first plate and third plate comprise a material selected from the group consisting of polydimethylsiloxane (PDMS), cyclic olefin copolymer (COC), polypropylene carbonate (PPC), polyether sulfone (PES), polyethylene terephthalate (PET), and a combination thereof, and the second plate comprises a thermoplastic resin or thermosetting resin material selected from the group consisting of polymethyl methacrylate (PMMA), cyclic olefin copolymer (COC), polyamide (PA), polyethylene (PE), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutylene terephthalate (PBT), fluorinated ethylene propylene (FEP), perfluoro alkoxyalkane (PFA), and a combination thereof.

10. The PCR device of claim 8, wherein a diameter of the through opening inlet unit of the third plate is selected in a range from about 1.0 mm to about 3.0 mm, a diameter of the through opening outlet units is selected in a range from about 1.0 mm to about 1.5 mm, a thickness of the third plate is selected in a range from about 0.1 mm to about 2 mm, a thickness of the second plate is selected in a range from about 100 µm to about 200 µm, a width of the through opening channel is selected in a range from about 0.5 mm to about 3 mm, and a length of the through opening channel is selected in a range from about 20 mm to about 40 mm.

11. The PCR device of claim 1, wherein the PCR device further comprises:
a light source emitting a light and disposed is further interposed between the first and second heating blocks; and
a light detection unit having a configuration to detect the light emitted from the light source, the light detection unit disposed between the first heating block and the second heating block,
wherein the control unit has a configuration to place the chip for PCR, by the driving unit, at a location between the light source and the light detection unit so that the light emitted from the light source transmits through the chip for PCR and is detected by the light detection unit.

12. The PCR device of claim 11, wherein the light detection unit is disposed above the driving unit interposing the driving unit and the chip for PCR between the light detection unit and the light source, and the driving unit further comprises a transmission unit for transmitting the light emitted from the light source to the light detection unit.

13. The PCR device of claim 11, wherein the PCR device further comprises:
a lens collecting the light emitted from the light source and coupled to the light source; and
a light filter filtering light at a range of a predetermined wavelengths, and coupled to the light source.

14. A polymerase chain reaction (PCR) device comprising:
a first heating block disposed on a substrate;
a second heating block separately disposed from the first heating block on the substrate;
a first temperature module coupled to a first heating wire to heat and maintain the first heating block at a first temperature in a range from about 90° C. to about 100° C.;
a second temperature module coupled to a second heating wire to heat and maintain the second heating block at a second temperature in a range from about 55° C. to about 75° C.;
a chip holder accommodating a chip for PCR;
a driving unit comprising,
a rail extending in a first direction between the first heating block and the second heating block, and
a connection member extending in a second direction and sliding along with the rail, the connection member accommodating the chip holder, wherein the first direction is different from the second direction;
a control unit coupled to the driving unit,
a light source emitting a light and disposed between the first and second heating blocks; and
a light detection unit having a configuration to detect the light emitted from the light source, the light detection unit disposed between the first heating block and the second heating block,
wherein the control unit has a configuration to place the chip for PCR, by the driving unit, at a location between the light source and the light detection unit so that the light emitted from the light source transmits through the chip for PCR and detected by the light detection unit,
wherein the control unit has a configuration to move the chip holder, by the driving unit, from the first heating block to the second heating block and from the second heating block to the first heating block,
wherein the control unit has a configuration to place the chip for PCR, by the driving unit, being alternately in contact with the first heating block and the second heating block for a first predetermined period of time for the first heating block and for a second predetermined period of time for the second heating block,
wherein each of the first heating block and the second heating block is a single heating block,
wherein the chip for PCR is detachably attached to the chip holder, and
wherein the light detection unit is disposed above the driving unit interposing the driving unit and the chip for PCR between the light detection unit and the light source, and the driving unit further comprises a transmission unit for transmitting the light emitted from the light source to the light detection unit.

* * * * *